United States Patent
Takahara et al.

(10) Patent No.: US 6,581,473 B2
(45) Date of Patent: Jun. 24, 2003

(54) METHOD FOR ANALYZING CREEP CHARACTERISTIC OF A PLASTIC MOLDED SUBSTANCE

(75) Inventors: Tadayoshi Takahara, Aichi-ken (JP); Jun Chen, Toyota (JP); Yoshio Sugimoto, Yokosuka (JP)

(73) Assignees: Toyota Jidosha Kabushiki Kaisha, Toyota (JP); Kanto Jidosha Kogyo Kabushiki Kaisha, Yokosuka (JP)

( * ) Notice: Subject to any disclaimer, the term of this patent is extended or adjusted under 35 U.S.C. 154(b) by 0 days.

(21) Appl. No.: 09/942,875

(22) Filed: Aug. 31, 2001

(65) Prior Publication Data

US 2003/0070491 A1 Apr. 17, 2003

(51) Int. Cl.$^7$ .................... G01N 11/00; G01D 1/16
(52) U.S. Cl. ................................. 73/788; 73/789
(58) Field of Search ................... 73/789, 794, 790, 73/788

(56) References Cited

U.S. PATENT DOCUMENTS

| | | | | |
|---|---|---|---|---|
| 4,033,181 A | * | 7/1977 | Oeser | 73/800 |
| 4,567,774 A | * | 2/1986 | Manahan et al. | 374/49 |
| 5,349,870 A | * | 9/1994 | Webber et al. | 374/47 |

FOREIGN PATENT DOCUMENTS

| | | | | |
|---|---|---|---|---|
| JP | 11-166884 | * | 5/1997 | ............ G01N/3/00 |
| JP | 11-166884 A | | 6/1999 | |

OTHER PUBLICATIONS

Sugimoto et al, "FEM Analysis of Heat Deformation of Plastic Bumper"; *Kanto Auto Works, LTD.*, pp. 135–138.

* cited by examiner

*Primary Examiner*—Hezron Williams
*Assistant Examiner*—Lilybett Martir
(74) *Attorney, Agent, or Firm*—Burns, Doane, Swecker & Mathis, LLP

(57) ABSTRACT

A method for analyzing creep characteristic of a plastic molded substance is provided wherein the creep characteristic can be analyzed of an actual plastic molded substance having various shape and fastening conditions with high precision. The main stress value for each section of the analysis target is read out, hydrostatic stress $\sigma_m$ of each section is calculated from the main stress value, and the stress condition is determined to be tensile stress when $\sigma_m$ is positive and to be compressive stress when $\sigma_m$ is negative. Tensile or compressive characteristic value is assigned based on the stress condition at each section, and creep is calculated for a predetermined time period based on the characteristic value. By employing characteristic values depending on the stress conditions of each section, precision of creep characteristic analysis is greatly enhanced.

4 Claims, 4 Drawing Sheets

METHOD FOR ANALYZING CREEP CHARACTERISTIC OF A PLASTIC MOLDED SUBSTANCE

BACKGROUND OF THE INVENTION

1. Field of the Invention

The present invention relates to an improvement in a method for analyzing the creep characteristic of a plastic molded substance.

2. Description of the Related Art

Conventional methods for analyzing creep characteristic of various molded substances are known wherein the creep characteristic is calculated by a finite element method based on a model such as a power multiple law or hyperbola law.

For example, described in Japanese Patent Laid-Open Publication No. Hei 11-166884 is an analysis method of a bending creep characteristic of a plastic molded substance in which the following Nutting's formula, being one of the power multiple laws, is employed.

$$d\epsilon_{cr}/dt = A\sigma^n t^m \tag{1}$$

In this equation, $\epsilon_{cr}$ represents creep strain, $\sigma$ represents stress, t represents elapsed time, and A, n, and m respectively represent constants defined by the material.

However, in the above conventional method for analyzing creep characteristic of a plastic molded substance, the same creep characteristic value, such as, for example, one set of creep characteristic value obtained from a bending test, is assigned to all the sections of the plastic molded substance, which is the analysis target. There therefore remains a problem that the creep characteristic cannot be precisely analyzed. This results from the fact that there are various shapes for the plastic molded substance, which is the analysis target, and hence, various stress conditions for each section of the plastic molded substance having different shapes or fastening conditions. Because creep characteristic values vary greatly according to the stress condition, assigning the same creep characteristic value to all of the sections results in inherently inaccurate estimates.

SUMMARY OF THE INVENTION

The present invention is conceived to solve the above problem, and one object of the present invention is to provide a creep characteristic analysis method for a plastic molded substance wherein the creep characteristic of an actual resin molded substance having various stress conditions due to different shapes or fastening conditions can be precisely analyzed.

In order to achieve at least the object above, according to one aspect of the present invention, provided is a method for analyzing creep characteristic of a plastic molded substance comprising the steps of calculating stress values for a substance or each section of a substance; determining stress condition at each section to be tensile or compressive based on the stress value; assigning a creep characteristic value to each section based on the determination result; and analyzing the creep characteristic after a predetermined time has elapsed using the creep characteristic values.

In the above method for analyzing creep characteristic of a plastic molded substance, it is preferable that the analysis result of the creep characteristic is reflected on the determination of the constraint condition or shape of the plastic molded substance.

In the above methods for analyzing creep characteristic of a plastic molded substance, it may also be preferable that the stress condition be determined to be tensile stress when the hydrostatic stress value is positive and the stress condition is determined to be compressive hydrostatic stress when the stress value is negative.

The method for analyzing creep characteristic of a plastic molded substance may be preferably applied to a finite element method.

DESCRIPTION OF THE PREFERRED EMBODIMENT

Figure 1:
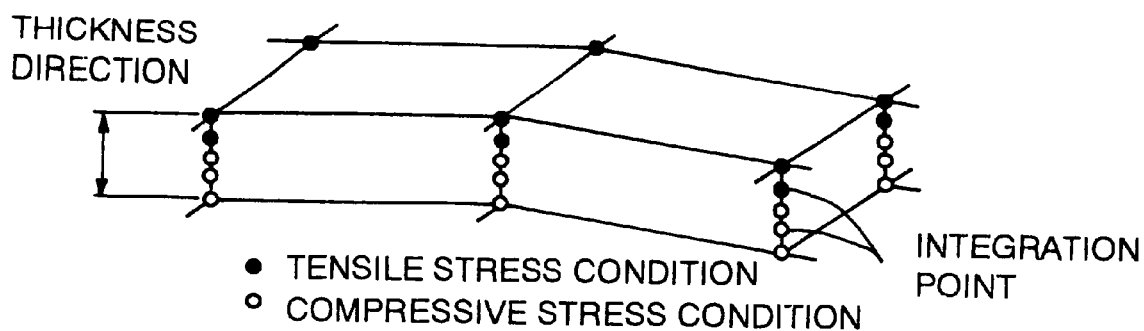
FIG. 1 is a diagram showing an example of a target for creep characteristic analysis.

A preferred embodiment of the present invention (hereinafter referred to as an "embodiment") will now be described referring to the drawings.

To analyze the creep characteristic of a plastic molded substance, creep for a predetermined time period is calculated by assigning a creep characteristic value to each section of the substance which is the analysis target. For example, when analysis is to be performed using a finite element method on a board-like substance shown in FIG. 1 as the analysis target, typically, integration points are defined in the thickness direction. Methods other than the finite element method, such as calculus of propositions and calculus of finite differences, may be employed.

When the substance shown in FIG. 1 is bent so that the board is concaved down in the thickness direction, the integration points at the upper side in the thickness direction (shown by ●) will be in a tensile stress condition and, similarly, the integration points at the lower side in the thickness direction (shown by ○) will be in a compressive stress condition.

Figure 2:
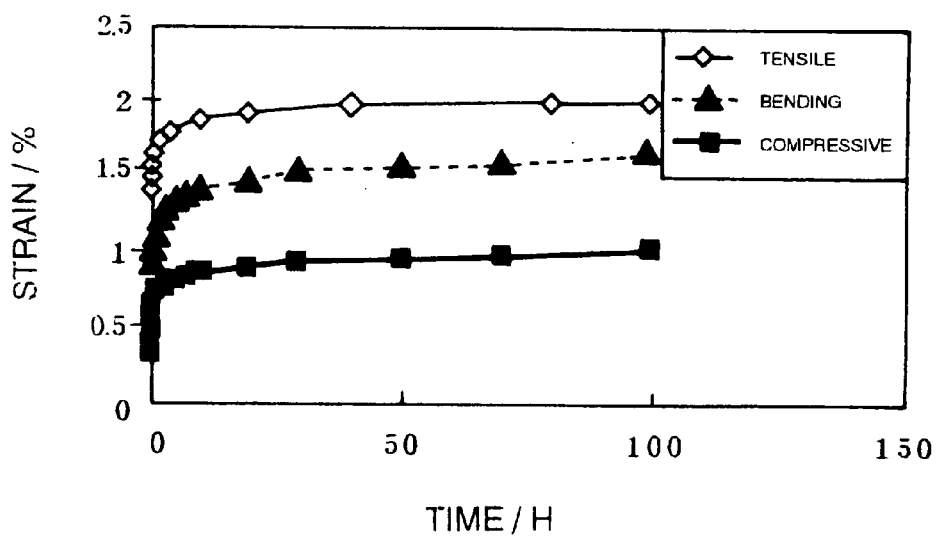
FIG. 2 is a diagram showing an example of the creep characteristic values of a plastic molded substance.

FIG. 2 shows, as "creep strain", the creep characteristic values after a predetermined time has elapsed of a plastic molded substance for cases where the stress condition is tensile, compressive, and typical bending. As shown in FIG. 2, when the analysis target is a plastic molded substance, the creep characteristics vary significantly according to the stress condition. Therefore, when any one of the characteristic values from among the tensile, compressive, and typical bending are assigned to all of the integration points without considering the stress condition, significant error is introduced into the analysis result of the creep characteristic. To address this problem, in the present invention, stress at each integration point is calculated, the stress condition is determined to be either tensile or compressive, and creep characteristic values based on the stress condition are assigned to each integration point. In this manner, high precision analysis for creep characteristic can be performed. For bending, such as the example shown in FIG. 1, because the stress is either tensile stress or compressive stress, there is no need to use a creep characteristic value specific to bending.

Figure 3:
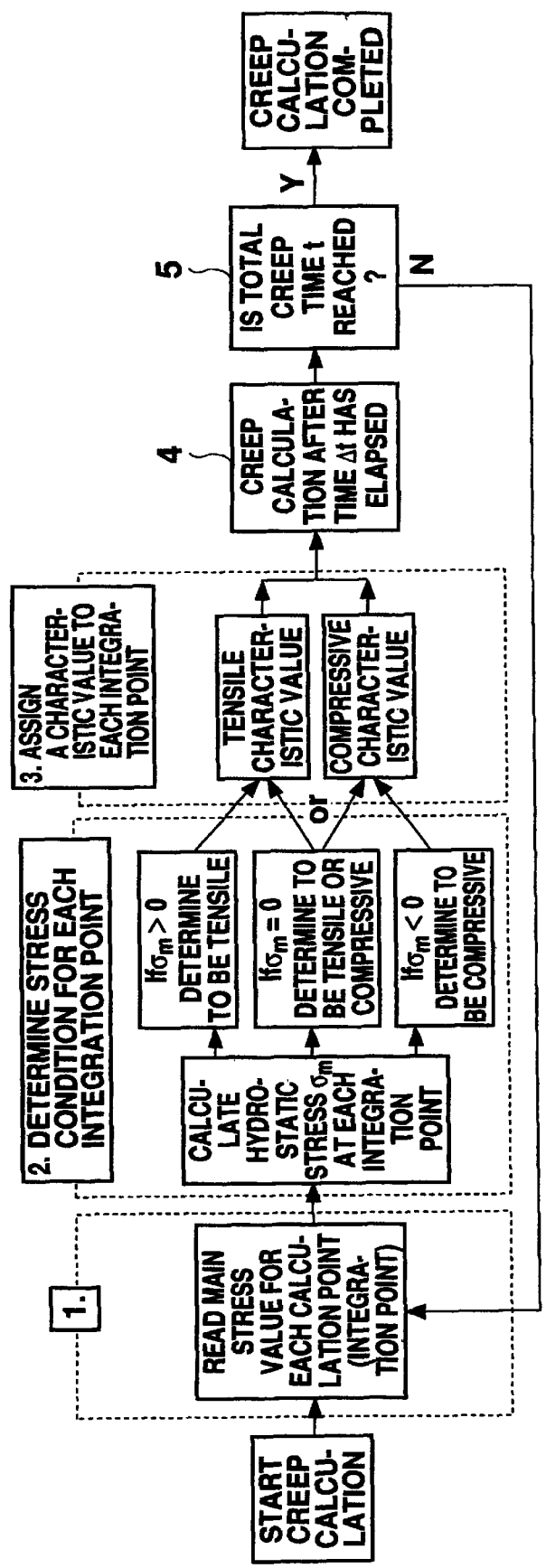
FIG. 3 is a diagram showing a preferred embodiment according to the present invention of a method for analyzing creep characteristic of a plastic molded substance.

FIG. 3 shows an embodiment according to the present invention of a method for analyzing creep characteristic of a plastic molded substance. As shown in FIG. 3, when the analysis is to be performed by a finite element method, a main stress value at each integration point defined on the analysis target is read out (first stage).

Then, a hydrostatic stress $\sigma_m$ is calculated at each integration point from the main stress value. If $\sigma_m$ is positive, the stress condition is determined to be tensile. If, on the other hand, $\sigma_m$ is negative, the stress condition is determined to be compressive. If $\sigma_m$ is zero, it is neither compressive or tensile, and thus, the stress can be considered either as compressive or tensile from the viewpoint of calculation. Because $\sigma_m$ is 0, strain is also 0, and thus, the result will not be affected (second stage).

For the integration point in which the stress condition is determined to be tensile, tensile characteristic value from among the creep characteristics is assigned to the integration point. Similarly, for the integration point in which the stress condition is determined to be compressive, compressive characteristic value is assigned (third stage).

After creep characteristic values are assigned to each of the integration points as described above, creep after a predetermined time ($\Delta t$) has elapsed is calculated using the respective creep characteristic values (fourth stage).

The processes from the first stage through the fourth stage are repeated until a total creep time t is reached. The creep after time t has elapsed is calculated as the integration value of the calculated value in the fourth stage (fifth stage). The creep calculation is thus completed.

In the method for analyzing creep characteristic of a plastic molded substance according to the present embodiment, the stress condition at each integration point is determined and the creep characteristic is calculated using the creep characteristic value corresponding to the stress condition. In this manner, the analysis precision of the creep characteristic can be improved compared to the case where creep characteristic values of a single type are assigned to all of the integration points.

Figure 4:
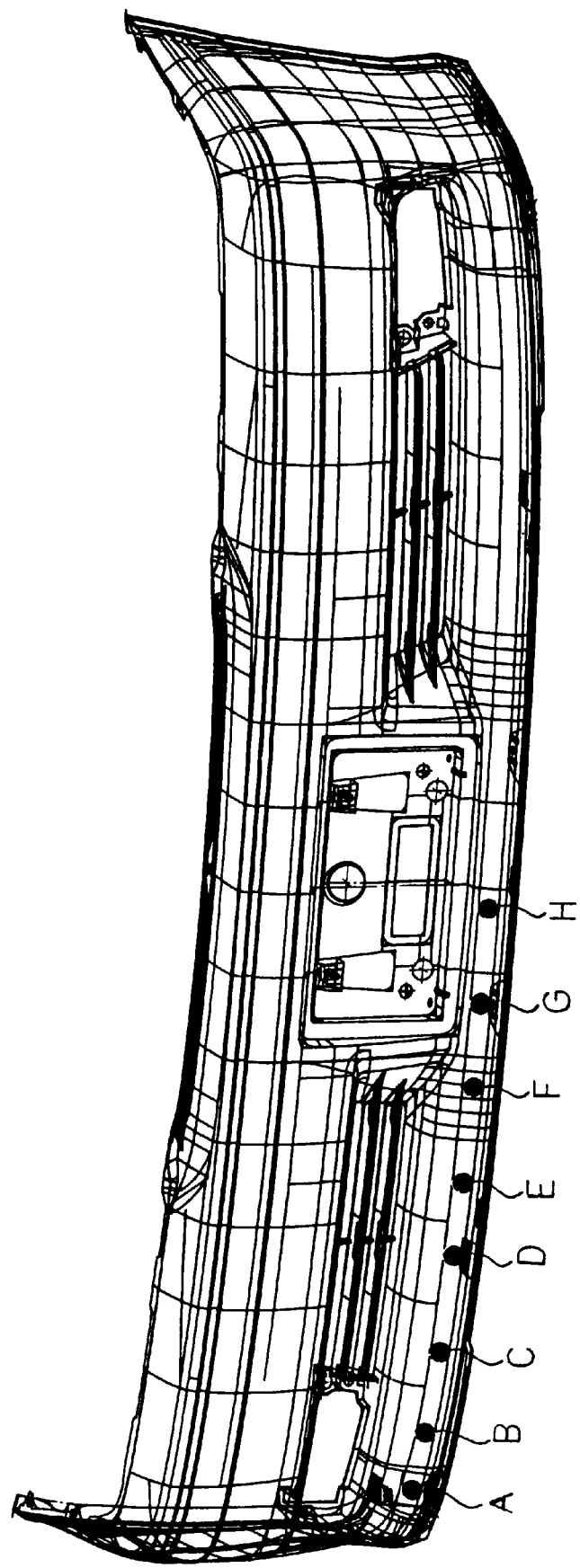
FIG. 4 is a diagram showing a plastic bumper fascia used for examination of the method for analyzing creep characteristic shown in FIG. 3.
Figure 5:
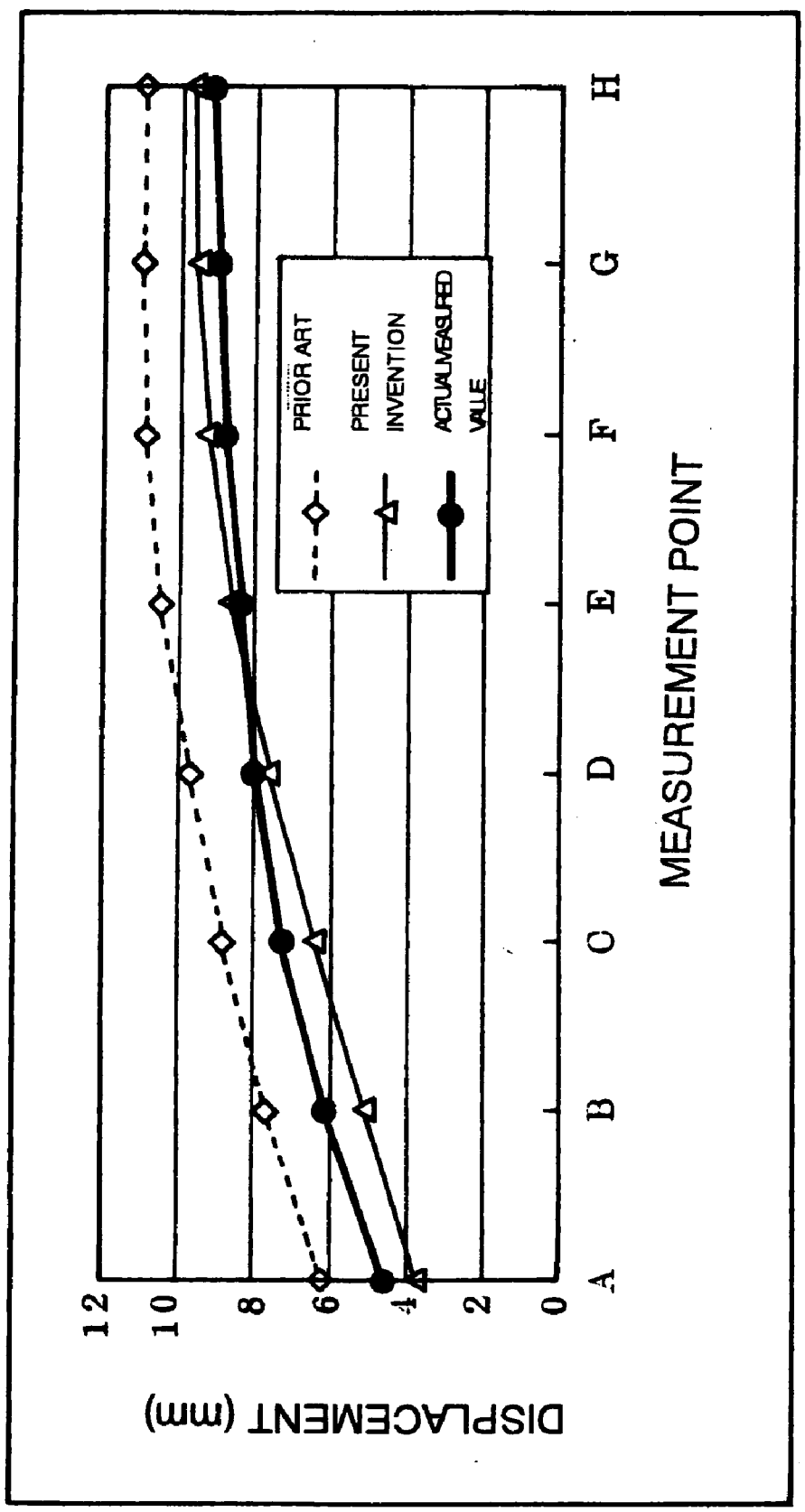
FIG. 5 is a diagram showing the analysis result of the creep characteristic of the plastic bumper fascia shown in FIG. 4.

FIG. 4 shows an example plastic automobile bumper fascia for examining the performance of the creep characteristic analysis method of a plastic molded substance according to the embodiment described above. In FIG. 4, eight points A through H are selected as measurement points, and analysis is performed on the displacement in thermal deformation. The result is shown in FIG. 5. The horizontal axis in FIG. 5 shows each measurement point and the vertical axis shows the displacement at each measurement point. In FIG. 5, the experimentally measured value of the displacement is shown by ●, the displacement calculated by the method of the present invention is shown by ∆, and the displacement calculated by the conventional method, that is, when one set of creep characteristic value obtained by a bending test is used, is shown by ◊. As is clear from FIG. 5, with the method of the present embodiment, a result which much close to the experimentally measured value is obtained. In contrast, results obtained employing the conventional method greatly differ from the experimentally measured value.

By considering the analysis result of the creep characteristic analysis method of a plastic molded substance according to the present embodiment when designing constraint conditions or shape of a plastic molded substance which is to be the final product, the performance of the product can be precisely predicted before the product is completed. It is possible to realize high quality designs based on the analysis results.

As described, according to the present invention, when the creep characteristic of a plastic molded substance is analyzed, creep characteristic value depending on the stress condition at each integration point is assigned. Therefore, the analysis precision of the creep characteristic can be improved.

Also, by reflecting the result obtained by the analysis method on the determination of the constraint conditions or shape, the performance can be precisely predicted without a physical mock-up. Moreover, with this additional information, the quality of the drawings can be improved.

What is claimed is:

1. A method for analyzing creep characteristic of a plastic molded substance comprising the steps of:

calculating a stress value for a substance or each section of a substance;

determining stress condition at each section to be tensile or compressive based on the stress value;

assigning a creep characteristic value to each section based on the determined stress condition at each section: and analyzing the creep characteristic after a predetermined time has elapsed using the creep characteristic values.

2. A method for analyzing creep characteristic of a plastic molded substance according to claim 1, wherein said analysis result of the creep characteristic is reflected on the determination of the constraint condition or shape of the plastic molded substance.

3. A method for analyzing creep characteristic of a plastic molded substance according to claim 1, wherein said stress condition is determined to be tensile stress when said stress value is positive and said stress condition is determined to be compressive stress when said stress value is negative.

4. A method for analyzing creep characteristic of a plastic molded substance according to claim 1, wherein said method is applied to a finite element method.

* * * * *